(12) United States Patent
Chung et al.

(10) Patent No.: US 8,980,844 B2
(45) Date of Patent: *Mar. 17, 2015

(54) PEPTIDE HAVING ANTIBACTERIAL OR ANTI-INFLAMMATORY ACTIVITY AND PHARMACEUTICAL COMPOSITION CONTAINING THE SAME AS AN ACTIVE INGREDIENT

(75) Inventors: Chong-Pyoung Chung, Seoul (KR); Yoon-Jeong Park, Seoul (KR); Jue-Yeon Lee, Gyeonggi-do (KR)

(73) Assignee: Nano Intelligent Biomedical Engineering Corporation Co. Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/703,565

(22) PCT Filed: Jun. 13, 2011

(86) PCT No.: PCT/KR2011/004300
§ 371 (c)(1),
(2), (4) Date: Dec. 11, 2012

(87) PCT Pub. No.: WO2011/159071
PCT Pub. Date: Dec. 22, 2011

(65) Prior Publication Data
US 2013/0210707 A1  Aug. 15, 2013

(30) Foreign Application Priority Data

Jun. 16, 2010  (KR) .................. 10-2010-0057000
Nov. 25, 2010  (KR) .................. 10-2010-0118184
Nov. 25, 2010  (KR) .................. 10-2010-0118185
Nov. 25, 2010  (KR) .................. 10-2010-0118186
Nov. 25, 2010  (KR) .................. 10-2010-0118187

(51) Int. Cl.
| | | |
|---|---|---|
| A61K 38/10 | (2006.01) |
| A61K 38/16 | (2006.01) |
| C07K 16/12 | (2006.01) |
| C07K 7/00 | (2006.01) |
| C07K 14/47 | (2006.01) |
| A61K 38/17 | (2006.01) |
| A61K 38/18 | (2006.01) |
| A61K 38/00 | (2006.01) |

(52) U.S. Cl.
CPC ............ C07K 14/4723 (2013.01); A61K 38/10 (2013.01); A61K 38/16 (2013.01); A61K 38/17 (2013.01); A61K 38/18 (2013.01); A61K 38/00 (2013.01)
USPC ......... 514/21.5; 514/2.4; 514/21.3; 514/21.4; 530/326; 530/325; 530/324

(58) Field of Classification Search
CPC ... A61K 38/10; A61K 38/16; C07K 14/4723; C07K 16/12; C07K 7/00
USPC ........ 514/21.5, 2.4, 21.3, 21.4; 530/326, 324, 530/325
See application file for complete search history.

(56) References Cited

U.S. PATENT DOCUMENTS

| | | | |
|---|---|---|---|
| 7,384,911 B2 | 6/2008 | Bulet et al. | |
| 7,566,447 B2 * | 7/2009 | Homan et al. | ............... 424/94.1 |
| 7,674,291 B2 | 3/2010 | Centanni et al. | |
| 2004/0072777 A1* | 4/2004 | Froelich et al. | .................. 514/44 |
| 2005/0014932 A1* | 1/2005 | Imboden et al. | ............. 530/350 |
| 2007/0093416 A1 | 4/2007 | Igarashi et al. | |

FOREIGN PATENT DOCUMENTS

| | | | | |
|---|---|---|---|---|
| CN | 1852708 A | 10/2006 | | |
| WO | WO 02/40512 | * | 5/2002 | ............. C07K 14/00 |

OTHER PUBLICATIONS

Machine translation of WO 02/40512, 2002.*
Xylitol from www.xlear.com/about-xylito-sweetener/xylitol-benefits, pp. 1-2. Accessed Mar. 17, 2004.*
Bauer, F., et al., "Structure determination of human and murine beta-defensins reveals structural conservation in the absence of significant sequence similarity", "Protein Science", Dec. 2001, pp. 2470-2479, vol. 10.
Brogden, K., "Antimicrobial peptides: pore formers or metabolic inhibitors in bacteria?", "Nat Rev Microbiol.", Feb. 10, 2005, pp. 238-250, vol. 3.
Dale, B., et al., "Antimicrobial Peptides in the Oral Environment: Expression and Function in Health and Disease", "Curr. Issues Mol. Biol.", Jul. 2005, pp. 119-134, vol. 7, No. 2.
Bulet, P., et al., "Sequence 10 from patent US 7384911", GenBank: Accession No. ACG82171.1, Aug. 18, 2008.
Centanni, J., et al., "Sequence 122 from patent US 7674291", GenBank: Accession No. ADF21100.1, Apr. 12, 2010.
Giacometti, A., et al., "Potential Therapeutic Role of Cationic Peptides in Three Experimental Models of Septic Shock", "Antimicrob. Agents Chemother.", Jul. 2002, pp. 2132-2136, vol. 46, No. 7.
Bauer, F., et al., "Chain A, Solution Structure of the Human Defensin Hbd-2", PDB: Accession No. 1E4Q_A, Jul. 10, 2009.
Rosenfeld, Y., et al., "Endotoxin (Lipopolysaccharide) Neutralization by Innate Immunity Host-Defense Peptides", "Journal of Biological Chemistry", Jan. 20, 2006, pp. 1636-1643, vol. 281, No. 3.
Scott, M., et al., "Interaction of Cationic Peptides with Lipoteichoic Acid and Gram-Positive Bacteria", "Infect. Immun.", Dec. 1999, pp. 6445-6453, vol. 67, No. 12.
Soerensen, O., et al., "Antimicrobial Peptides in Innate Immune Responses", "Contrib Microbiol.", 2008, pp. 61-77, vol. 15.

* cited by examiner

Primary Examiner — Julie Ha
(74) Attorney, Agent, or Firm — Hultquist, PLLC; Mary B. Grant

(57) ABSTRACT

A peptide having antibacterial or anti-inflammatory activity and a pharmaceutical composition containing the same as an active ingredient are described. Also, a peptide having antibacterial or anti-inflammatory activity against dental bacteria, including periodontal pathogens, and bacteria causing atopic dermatitis, and a pharmaceutical composition containing the peptide as an active ingredient are described. The inventive peptide having antibacterial or anti-inflammatory activity can be used for the treatment of both dental infectious diseases, including periodontitis, and inflammations, including arthritis.

8 Claims, 4 Drawing Sheets

SEQUENCE LISTING

```
<160> NUMBER OF SEQ ID NOS: 4

<210> SEQ ID NO 1
<211> LENGTH: 22
<212> TYPE: PRT
<213> ORGANISM: Artificial Sequence
<220> FEATURE:
<223> OTHER INFORMATION: BD2-2

<400> SEQUENCE: 1

Cys Pro Arg Arg Tyr Lys Gln Ile Gly Thr Cys Gly Leu Pro Gly Thr
1               5                   10                  15

Lys Cys Cys Lys Lys Pro
            20

<210> SEQ ID NO 2
<211> LENGTH: 15
<212> TYPE: PRT
<213> ORGANISM: Artificial Sequence
<220> FEATURE:
<223> OTHER INFORMATION: BD3-3

<400> SEQUENCE: 2

Gly Lys Cys Ser Thr Arg Gly Arg Lys Cys Cys Arg Arg Lys Lys
1               5                   10                  15

<210> SEQ ID NO 3
<211> LENGTH: 18
<212> TYPE: PRT
<213> ORGANISM: Artificial Sequence
<220> FEATURE:
<223> OTHER INFORMATION: PDGF

<400> SEQUENCE: 3

Arg Lys Ile Glu Ile Val Arg Lys Lys Pro Ile Phe Lys Lys Ala Thr
1               5                   10                  15

Val Thr

<210> SEQ ID NO 4
<211> LENGTH: 22
<212> TYPE: PRT
<213> ORGANISM: Artificial Sequence
<220> FEATURE:
<223> OTHER INFORMATION: HB-EGF

<400> SEQUENCE: 4

Cys Lys Arg Lys Lys Lys Gly Lys Gly Leu Gly Lys Lys Arg Asp Pro
1               5                   10                  15

Cys Leu Arg Lys Tyr Lys
            20
```

PEPTIDE HAVING ANTIBACTERIAL OR ANTI-INFLAMMATORY ACTIVITY AND PHARMACEUTICAL COMPOSITION CONTAINING THE SAME AS AN ACTIVE INGREDIENT

CROSS-REFERENCE TO RELATED APPLICATIONS

This application is a U.S. national phase application under the provisions of 35 U.S.C. §371 of International Patent Application No. PCT/KR2011/004300 filed Jun. 13, 2011, which in turn claims priority of Korean Patent Application No. 10-2010-0057000 filed Jun. 16, 2010, Korean Patent Application No. 10-2010-0118187 filed Nov. 25, 2010, Korean Patent Application No. 10-2010-0118186 filed Nov. 25, 2010, Korean Patent Application No. 10-2010-0118185 filed Nov. 25, 2010, and Korean Patent Application No. 10-2010-0118184 filed Nov. 25, 2010. The disclosures of such international patent application and Korean priority patent applications are hereby incorporated herein by reference in their respective entireties, for all purposes.

TECHNICAL FIELD

The present invention relates to a peptide having antibacterial or anti-inflammatory activity and a pharmaceutical composition containing the same as an active ingredient, and more particularly to a peptide having antibacterial or anti-inflammatory activity against dental bacteria, including periodontal pathogens, and bacteria causing atopic dermatitis, and to a pharmaceutical composition containing the peptide as an active ingredient.

BACKGROUND ART

Periodontal disease is a disease wherein soft tissue around teeth and alveolar bone are destroyed by chronic inflammation caused by periodontal pathogens, so that the gum bleeds and teeth are loose and ultimately lost. Periodontal pathogens include *Prevotella intermedia, Actinomyces israelii, Fusobacterium nucleatum*, etc.

Efforts have been made continuously to eliminate plaque-forming bacteria using antibiotics such as penicillin in order to prevent periodontal disease. However, these antibiotics are not used in clinical practice because of antibiotic-resistant bacteria created when these antibiotics are used for a long period of time. To overcome this disadvantage, various methods including the use of fluorine-based compounds or automatic dental cleaning devices have been developed, but the effects thereof are insignificant. In clinical practice, a mouthwash containing chlorohexidine is used. In addition, plasters, ointments and the like, which contain minocycline, are used.

Meanwhile, atopic dermatitis is a disease that is widely distributed worldwide, and 3-5% of children 5 years old or younger are suffering from this disease. In general, atopic dermatitis begins in infancy and childhood, 90% or more of patients with atopic dermatitis show symptoms before the age of 5 years.

In the past, atopic dermatitis was thought as a kind of allergy. However, as the consideration of atopic dermatitis in terms of non-allergy is expanded, an approach to the cause and solution of eczema reactions is being made. In a process of examining various skin physiological functions in patients having this disease, the patients show abnormal functions, including a reduction in perspiration, a reduction in sebum secretion, an abnormal skin vascular reaction and a dry skin. Thus, in terms of non-allergy, a new opinion that a dry skin is most significant as the condition of atopic dermatitis is being suggested.

When a dry skin is formed, the barrier function of the skin surface will be lost, the penetration of external stimuli or allergens into the skin will be easy, and the skin will have rejection reaction to the penetrated materials. Atopic dermatitis leads to severe symptoms due to secondary bacterial infection caused by scratching of an itchy skin area. Atopic patients have a high possibility of exposure to bacterial infection as a result of long-term scratching and being dried. Main bacteria that cause secondary bacterial infection in atopic dermatitis patients are Streptococcus bacteria, and several kinds of microorganisms infect atopic dermatitis patients to cause reactions such as inflammation. Recent reports indicate that the endotoxin of such bacteria stimulates the immune system of the human body to release allergy-causing chemicals, thereby worsening atopic dermatitis. In other words, these bacteria themselves act as allergens.

Patients having atopic skin symptoms are treated with steroid ointments and internal medicines (including injectable solutions) in hospitals and pharmacies. However, it is known that the use of steroids as internal medicines or injectable solutions causes skin adverse effects, including subcutaneous congestion, pigmentation, hair loss, itching, and facial erythma, adverse effects in the endocrine system, including secondary adrenocortical insufficiency and diabetes, adverse effects in the digestive system, including peptic ulcer and gastritis, adverse effects in the psychoneural system, including melancholia and headache, adverse effects musculoskeletal system, including osteoporosis, adverse effects of protein metabolism, including nitrogen imbalance, adverse effects in the electrolyte system, including a rise in blood pressure, and adverse effects in the eye, including ocular hypertension and glaucoma. In addition, it was reported that the use of steroid-based ointments causes severe adverse effects, including skin infection, steroidal acne, steroidal dermatitis, and the inhibition of pituitary-adrenal function.

Particularly, it is evident that the adverse effects of steroids in infant patients are very severe compared to those in adults. Due to such adverse effects, there are increasing attempts to find new methods for treating atopic dermatitis. In addition to the use of medicines, cosmetics for atopic dermatitis are being used, and these products are being actively developed. The first generation products for atopic dermatitis were based on natural oils and mineral components, and the second generation products mainly contain ceramide and natural moisturizing factors. However, the first and second generation products focus on the maintenance of skin moisture, and thus there is a limitation in improvement of atopic skin. Thus, it is essential that proper antibiotic substances is used for the treatment of atopic dermatitis.

Accordingly, the present inventors have made extensive efforts to develop a peptide having antibacterial or anti-inflammatory activity against periodontal pathogens and skin parasitic bacteria, and as a result, have found that a peptide derived from human beta-defensin, platelet-derived growth factor or heparin-binding epidermal growth factor is effective for the treatment of periodontal disease and the alleviation of atopic dermatitis, thereby completing the present invention.

DISCLOSURE OF INVENTION

It is an object of the present invention to provide a peptide having antibacterial or anti-inflammatory activity.

Another object of the present invention is to provide a pharmaceutical composition containing the above peptide as an active ingredient.

To achieve the above objects, the present invention provides a peptide derived from human beta-defensin, platelet-derived growth factor or heparin-binding epidermal growth factor, which has antibacterial or anti-inflammatory activity.

The present invention also provides an antibacterial composition containing the above peptide as an active ingredient.

The present invention also provides a composition for treating inflammation, which contains the above peptide as an active ingredient.

BEST MODE FOR CARRYING OUT THE INVENTION

Figure 1:
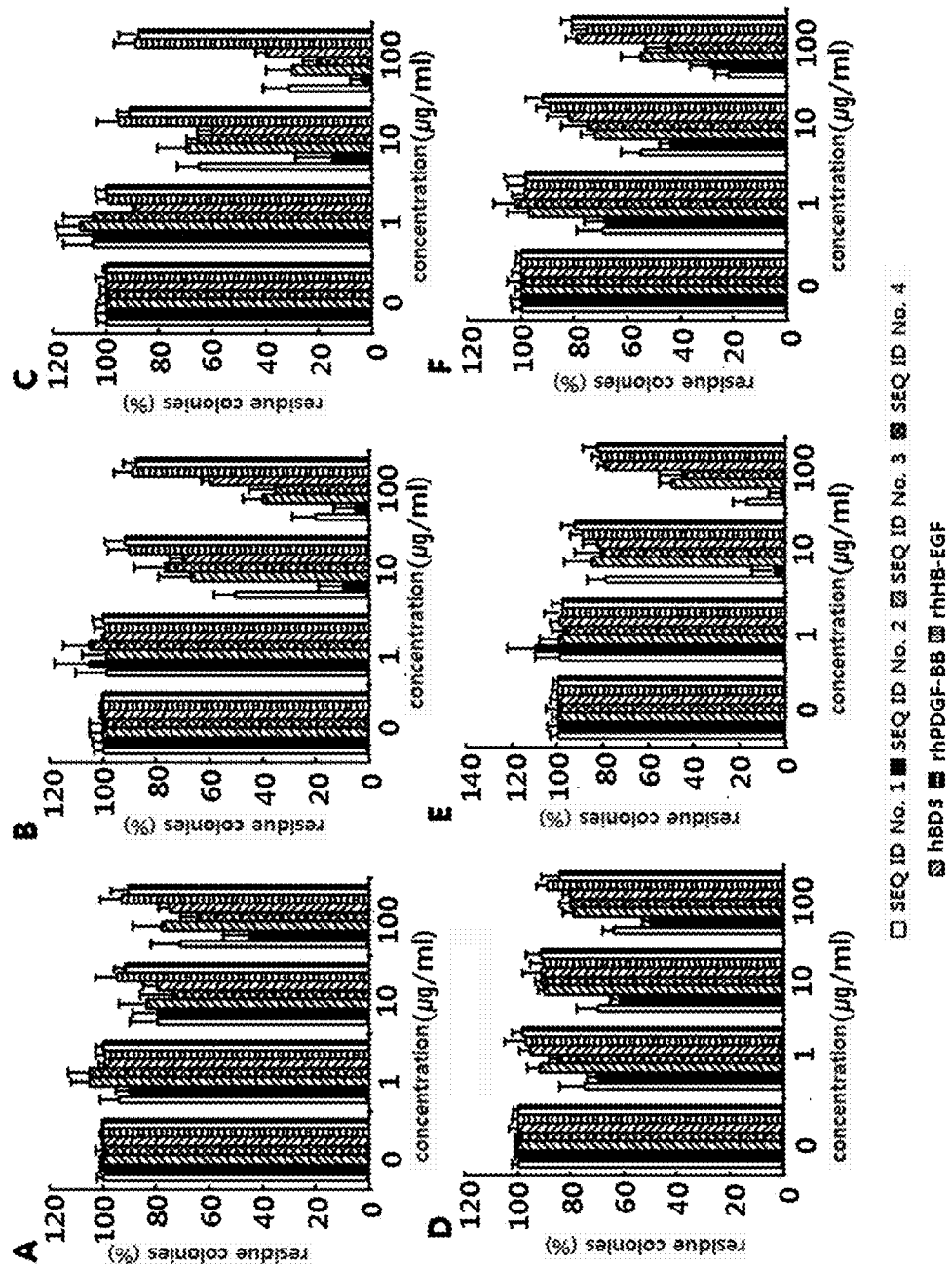
FIG. 1 shows the results of measuring the antibacterial activities of peptides having amino acid sequences of SEQ ID NOS: 1 to 4 using a liquid dilution method, wherein A: *Prevotella intermedia*; B: *Actinomyces israelii*; C: *Fusobacterium nucleatum*; D: *Staphylococcus aureus*.subsp.*aureus*; E: *Streptococcus pyogenes*; and F: *Staphylococcus epidermidis*.

Unless defined otherwise, all technical and scientific terms used herein have the same meaning as commonly understood by one of ordinary skill in the art to which the invention pertains. Generally, the nomenclature used herein and the experiment methods which will be described later are those well known and commonly employed in the art.

The present invention is directed to a peptide which has antibacterial or anti-inflammatory activity and amino acid sequences of SEQ ID NOS: 1 to 4.

Antibacterial peptides exist in the innate immune system of humans, bind to the cell membrane and perforate the cell membrane, thereby exhibiting a wide range of antibacterial activities against bacteria, fungi and viruses (Brogden K A. *Nat Rev Microbiol*, 3:238, 2005; Sørensen O E. et al., *Contrib Microbiol*, 15:61, 2008).

Among these peptides, any peptides also function to neutralize the activity of lipopolysaccharide (LPS) (Rosenfeld Y et al., *J Biol Chem*, 281:1636, 2006).

Antibacterial peptides are produced in various cells, which are associated with infection, including epithelial cells, neutrophils and salivary gland. These antibacterial peptides include human defensin, cathelicidin LL-37, histatin and the like, which are cationic and hydrophobic. Cationic peptides are known to prevent septicemia and inflammation from being caused by gram-negative or gram-positive bacteria (Scott M G. et al., *Infect Immun*, 67:6445, 1999; Giacometti A. et al., *Antimicrob Agents Chemother*, 46:2132, 2002).

The inventive peptide having antibacterial or anti-inflammatory activity is a peptide fragment derived from human beta-defensin-2 (hBD2), human beta-defensin-3 (hBD3), human platelet derived growth factor-B (PDGF-B) or heparin-binding epidermal growth factor (HB-EGF). The peptide derived from human beta-defensin-2 has an amino acid sequence of SEQ ID NO: 1, and the peptide derived from human beta-defensin-3 has an amino acid sequence of SEQ ID NO: 2. In addition, the peptide derived from human platelet derived growth factor-B has an amino acid sequence of SEQ ID NO: 3, and the peptide derived from heparin-binding epidermal growth factor has an amino acid sequence of SEQ ID NO: 4.

The amino acid sequences of SEQ ID NOS: 1 to 4 are as follows:

```
(BD2-2):
                                          SEQ ID NO: 1
C-P-R-R-Y-K-Q-I-G-T-C-G-L-P-G-T-K-C-C-K-K-P (BD3-3):
                                          SEQ ID NO: 2
G-K-C-S-T-R-G-R-K-C-C-R-R-K-K (PDGF):
                                          SEQ ID NO: 3
R-K-I-E-I-V-R-K-K-P-I-F-K-K-A-T-V-T (HB-EGF):
                                          SEQ ID NO: 4
C-K-R-K-K-K-G-K-G-L-G-K-K-R-D-P-C-L-R-K-Y-K
```

In one embodiment of the present invention, it was found that the peptides having the amino acid sequences of SEQ ID NOS: 1 to 4 have excellent antibacterial activities against typical periodontal pathogens, including *Prevotella intermedia*, *Actinomyces israelii*, and *Fusobacterium nucleatum*, and skin parasitic bacteria capable of causing atopic dermatitis, including *Staphylococcus aureus* subsp *aureus*, *Staphylococcus epidermidis*, and *Streptococcus pyogenes*. In addition, it was shown that the peptides of the present invention have excellent antibacterial effects compared to hBD3, rhPDGF-BB (recombinant human PDGF-BB) and rhHB-EGF (recombinant human HB-EG).

In another embodiment of the present invention, in order to evaluate anti-allergic effects capable of alleviating itching that is the symptom of atopic dermatitis, the changes in release of β-hexosaminidase (degranulation-related enzyme) by the peptides having the amino acid sequences of SEQ ID NOS: 1 to 4 were measured and compared with the changes in release of β-hexosaminidase by KF (ketotifen fumarate), hBD3, rhPDGF-BB (recombinant human PDGF-BB) and rhHB-EGF (recombinant humanHB-EG), which are agents for treating allergic diseases. As a result, it was found that the peptides having the amino acid sequences of SEQ ID NOS: 1 to 4 have excellent effects on the inhibition of release of β-hexosaminidase.

In still another embodiment of the present invention, the inhibitory effects of the peptides having the amino acid sequences of SEQ ID NOS: 1 to 4 on the expression of NF-κB, iNOS and COX-2 were examined by Western blot analysis. As a result, it was found that the peptides having the amino acid sequences of SEQ ID NOS: 1 to 4 inhibit the LPS-induced expression of NF-κB, iNOS and COX-2. In addition, it was found that the inhibitory effects of KF (ketotifen fumarate), hBD3, rhPDGF-BB (recombinant human PDGF-BB) and rhHB-EGF (recombinant human HB-EGF), which are used as agents for treating allergic diseases, on the expression of NF-κB, iNOS and COX-2, are smaller than the inhibitory effects of the peptides having the amino acid sequences of SEQ ID NOS: 1 to 4.

In another aspect, the present invention is directed to an antibacterial composition containing any one of the peptides having amino acid sequences of SEQ ID NOS: 1 to 4 as an active ingredient.

The antibacterial composition according to the present invention may be a composition for treating dental infectious disease. Herein, the dental infectious disease may be selected from the group consisting of gingivitis, periodontitis, and peri-implantitis.

In the present invention, the composition for treating dental infectious disease may contain the peptide in an amount of $10^{-3}$ to 1 part by weight, and preferably $10^{-2}$ to $10^{-1}$ parts by weight, based on the total weight of the composition. If the content of the peptide in the composition is less than $10^{-3}$ parts by weight, the antibacterial or anti-inflammatory effect of the composition will be insignificant, and if the content of the peptide is more than 1 part by weight, the composition will show no further increase in the antibacterial or anti-inflammatory effect.

In the present invention, the composition for treating dental infectious disease may further contain one or more selected from the group consisting of propolis, xylitol and protease. Herein, propolis or xylitol can improve the sensory characteristics of the composition, and the addition of protease can improve the antibacterial effect and lipopolysaccharide-removing effect of the composition.

In the present invention, the composition for treating dental infectious disease may contain a pharmaceutically acceptable carrier which is selected from the group consisting of excipients such as starch, lactose, calcium carbonate or calcium phosphate, binders such as starch, gum Arabia, carboxymethyl cellulose, hydroxymethyl cellulose or crystalline cellulose, lubricants such as magnesium stearate or talc, disintegrants such as calcium carboxymethylcellulose, talc or synthetic aluminum silicate, diluents such as water or vegetable oil, and mixtures thereof.

The inventive composition for treating dental infectious disease may be formulated in the form of powders, fine granules, liquids, sprays, ointments and gels, but is not limited thereto. Most preferably, the composition is formulated in the form of gels.

In still another aspect, the present invention is directed to a composition for treating inflammation, which contains any one of the peptides having amino acid sequences of SEQ ID NOS: 1 to 4 as an active ingredient.

In the present invention, the inflammation may be selected from atopy, psoriasis, arthritis, dermatitis, allergy, osteoarthritis, nasitis, otitis media, a sore throat, tonsillitis, cystitis, and nephritis.

In the present invention, the composition for treating inflammation may contain the peptide in an amount of $10^{-2}$ to 10 parts by weight, and preferably $10^{-1}$ to 1 part by weight, based on the total weight of the composition. If the content of the peptide in the composition is less than $10^{-2}$ parts by weight, the antibacterial or anti-inflammatory effect of the composition will be insignificant, and if the content of the peptide is more than 10 parts by weight, the composition will show no further increase in the antibacterial or anti-inflammatory effect.

In addition, the peptide in the composition for treating inflammation can be formulated with conventional components according to a conventional method. For example, it may be formulated as lotion, cream, ointments, emulsions, foundations, oils, packs, soaps (including medicinal soap), body soaps, lipsticks, nail cosmetics, eye cosmetics, perfume, facial washes, mouth washes, tooth paste, deodorants, bath products, shampoo, rinses, hair tonics, hair sprays, hair colors, and the like. In addition, the composition of the present invention may be optionally formulated in the form of solutions, creams, pastes, gels, sols, foams, solids, patch, or powders.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Measurement of Antibacterial Activities of Peptides

In order to evaluate the antibacterial effects of the peptides having the amino acid sequences of SEQ ID NOS: 1 to 4, measurement of the antibacterial activities of the peptides was carried out using a liquid dilution method. Periodontal pathogens, including *Prevotella intermedia, Actinomyces israelii*, and *Fusobacterium nucleatum*, were cultured in tryptic soy broth. *Staphylococcus aureus* subsp *aureus* and *Streptococcus pyogenes* were curtured in trypticase soy broth, and *Staphylococcus epidermidis* was curtured in nutrient liquid medium. After the above bacterial strains had been cultured until the absorbance at 620 nm reached 1, the cells were collected and used in the test. The collected bacterial cells were diluted with PBS to a concentration of $10^5$-$10^7$ cells per ml, and the diluted cells were plated on a TSA (tryptic soy agar) plate and cultured at 37° C. for 24 hours.

In order to measure the antibacterial activities of the peptides using the liquid dilution method, 1 ml of distilled water was placed in a fine tube, after which 10 µl of the diluted bacterial cell solution was placed in the tube, and then 50 µl of the solution was plated on plate medium and used as a control. Meanwhile, plate medium was treated with each of the antibacterial peptides at concentrations of 1 µg/ml, 10 µg/ml and 100 µg/ml at 37° C. for 1 hours, after which 50 µl of the bacterial cell solution was plated on the plate medium, and the number of colonies produced was counted. In the same manner, the antibacterial activities of growth factors, including hBD3, rhPDGF-BB (recombinant human PDGF-BB) and rhHB-EGF (recombinant human HB-EG), were measured and compared with those of the peptides of the present invention.

As a result, as can be seen in FIG. 1, the peptides having the amino acid sequences of SEQ ID NOS: 1 to 4 showed the highest antibacterial activity at a concentration of 100 µg/ml, and the antibacterial activities of the growth factors (hBD3, rhPDGF-BB and rhHB-EGF) were lower than those of the peptides having the amino acid sequences of SEQ ID NOS: 1 to 4.

Example 2

Evaluation of Anti-allergic Effects of Peptides at the Cell Level

In order to examine the anti-allergic effects of the peptides having the amino acid sequences of SEQ ID NOS: 1 to 4, the changes in release of β-hexosaminidase by the peptides were measured.

Basophilic leukemia RBL-2H3 cells obtained from ATCC (American Type Culture Collection) were cultured in a $CO_2$ incubator (supplied with 5% $CO_2$ and 95% air) with DMEM (Dulbecco's modified Eagle medium) medium containing 10% FBS (heat inactivated fetal bovine serum) and 100 units/ml of antibiotics (penicillin and streptomycin) at 37° C. for 24 hours. Specifically, the cells were cultured in a 96-well plate at a density of $5\times10^4$ cells/well, and then the supernatant was removed. Then, 100 µl of DMEM containing 100 ng/ml of anti-DNP IgE was added to each well of the plate and cultured at 37° C. for 24 hours. Then, the plate was washed once with PBS, and 100 µl of Tyrode's buffer was added to each well and cultured for 15 minutes. Each of the peptides having the amino acid sequences of SEQ ID NOS: 1 to 4 was diluted with Tyrode's buffer to various concentrations (1, 10 and 100 µg/ml), and 100 µl of the dilution was added to each well and reacted at 37° C. for 1 hours. 100 µl of DNP-HAS (100 ng/ml) was added to each well and reacted at 37° C. for 1 hour. After the cultivation, 80 µl of the supernatant was taken and added to another 96-well plate, and the same volume of a substrate solution (0.2M citrate, 1 mM p-nitrophenyl-β-acetyl-glucosamide, pH 4.5) was added thereto and reacted for hour. During 1 hour of the reaction, the cells were treated with lysis buffer (1% Triton X-100) and centrifuged at 4° C. at 12,000 g for 5 minutes, and the supernatant was added to a fresh 96-well plate and reacted in the same manner as described above. 100 µl of a reaction stop buffer (0.2M sodium bicarbonate, pH 10) was added to each well in order to stop the substrate reaction and was reacted for 5 minutes. Then, the absorbance at 405 nm was measured and the change in release of β-hexosaminidase was determined. The method of measuring the amount of β-hexosaminidase is known to be sensitive and accurate compared to a method of quantifying histamine, and thus has recently been frequently used in studies on degranulation. For comparison, In addition, the changes in release of β-hexosaminidase by KF and growth factors (hBD3, rhPDGF-BB and rhHB-EGF), which are used as agents for treating allergic diseases, were measured in the same manner as described above and compared with the changes caused by the peptides.

Figure 2:
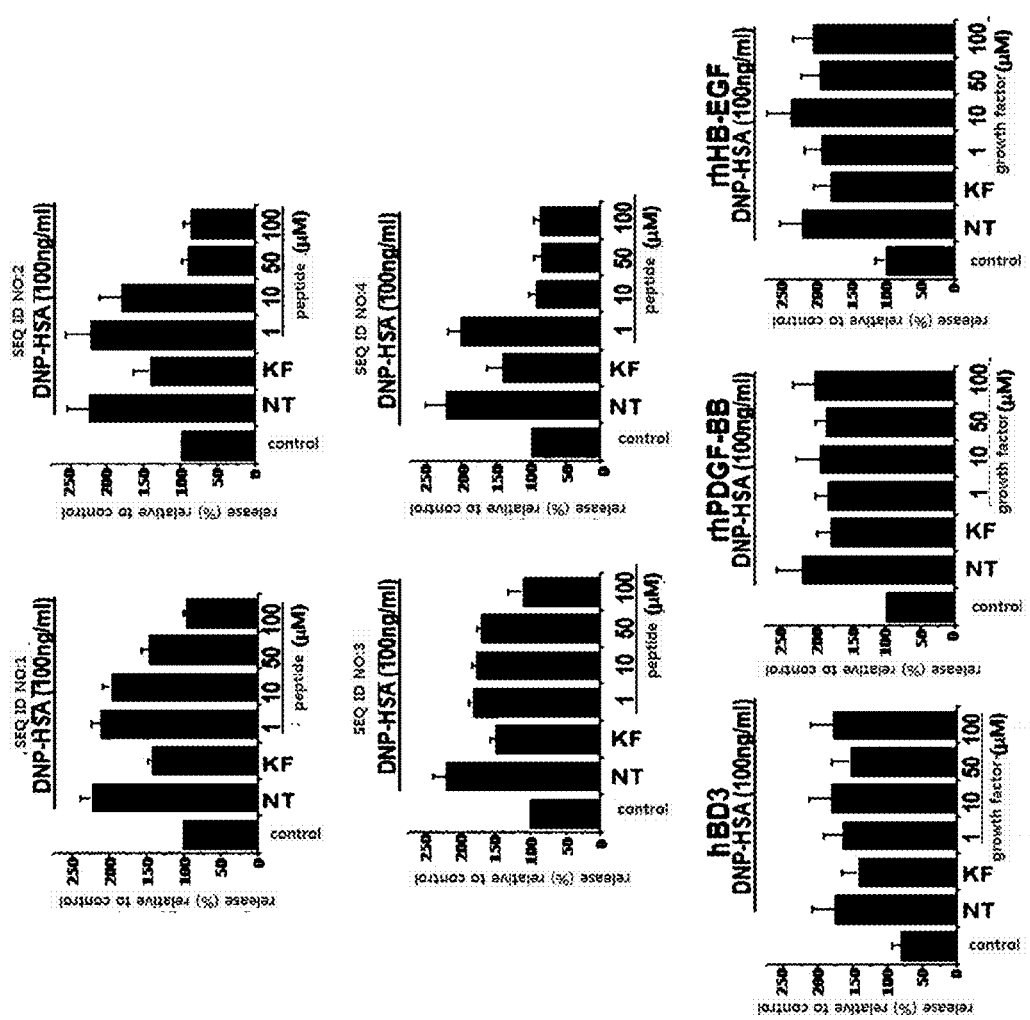
FIG. 2 is a set of graphs showing the results of measurement of the changes in release of β-hexosaminidase by peptides having amino acid sequences of SEQ ID NOS: 1 to 4.

As a result, as can be seen in FIG. 2, the peptides having the amino acid sequences of SEQ ID NOS: 1 to 4 showed a reduction in the release of β-hexosaminidase at a concentration of 100 µM to a level similar to that of the control, whereas hBD3, rhPDGF-BB and rhHB-EGF did not influence the reduction in the release of β-hexosaminidase.

Example 3

Evaluation of Anti-inflammatory Effects of Peptides at the Cell Level

1) Western Blot Analysis of NF-κB

In order to examine association with signals, the expression of the allergic inflammation-associated enzyme NF-κB associated with the NF-κB signal was measured.

RAW 264.7 cells obtained from ATCC (American Type Culture Collection) were incubated in a $CO_2$ incubator (supplied with 5% $CO_2$ and 95% air) with DMEM (Dulbecco's modified Eagle medium) medium containing 10% FBS and 100 units/ml of antibiotics (penicillin and streptomycin) at 37° C.

The incubated RAW 264.7 cells were treated with each of the peptides having the amino acid sequences of SEQ ID NOS: 1 to 4 for 1 hour, and then treated with LPS (10 ng/ml). After 8 hours, a protein of each of the cytosol and the nucleus was collected and compared with the changes in expression of NF-κB caused by hBD3, rhPDGF-BB and rhHB-EGF. The collected protein was identified by SDS-PAGE and transferred to a nitrocellulose membrane using a blotting kit. The membrane was blotted with the primary antibody NF-κB and exposed to HRP (horseradish peroxidase)-conjugated secondary antibody. Then, the membrane was allowed to react with an ECL western blot detection reagent and exposed to an X-ray film to detect a signal, thereby measuring the expression of the inflammation-associated enzyme NF-κB.

Figure 3:
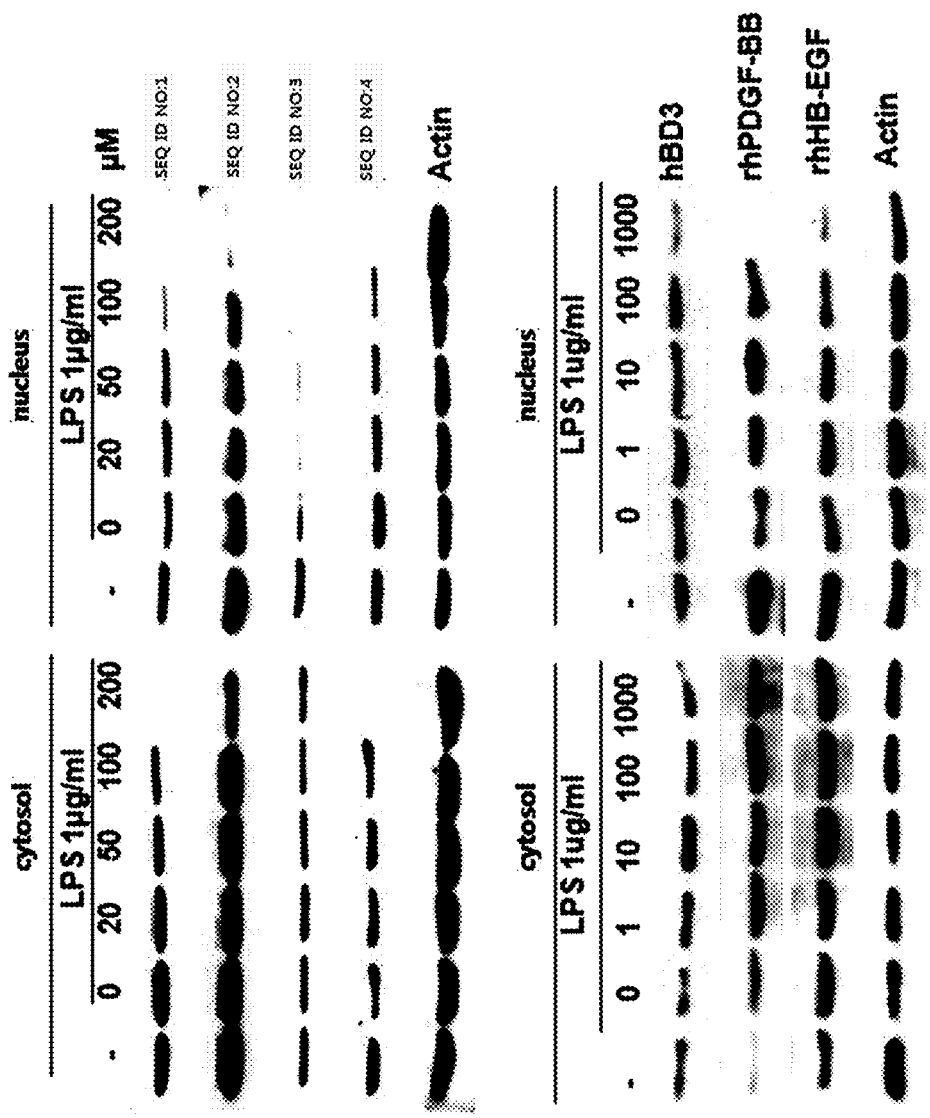
FIG. 3 shows the results of Western blot analysis of NF-κB.

As a result, as can be seen in FIG. 3, the peptides having the amino acid sequences of SEQ ID NOS: 1 to 4 inhibited the LPS-induced expression of NF-κB, but the inhibitory effects of hBD3, rhPDGF-BB and rhHB-EGF on the expression of NF-κB were not greater than those of the peptides.

2) Western Blot Analysis of iNOS and COX-2

RAW 264.7 cells obtained from ATCC (American Type Culture Collection) were incubated in a $CO_2$ incubator (supplied with 5% $CO_2$ and 95% air) with DMEM (Dulbecco's modified Eagle medium) medium containing 10% FBS and 100 units/ml of antibiotics (penicillin and streptomycin) at 37° C.

The incubated RAW 264.7 cells were treated with each of the peptides having the amino acid sequences of SEQ ID NOS: 1 to 4 for 1 hour, and then treated with LPS (10 ng/ml). After 8 hours, a protein of each of the cytosol and the nucleus was collected and compared with the changes in expressions of iNOS and COX-2 caused by hBD3, rhPDGF-BB and rhHB-EGF. The collected protein was identified by SDS-PAGE and transferred to a nitrocellulose membrane using a blotting kit. The membrane was blotted with each of the primary antibodies iNOS and COX-2 and exposed to HRP (horseradish peroxidase)-conjugated secondary antibody. Then, the membrane was allowed to react with an ECL western blot detection reagent and exposed to an X-ray film to detect signals, thereby measuring the expressions of the inflammation-associated enzymes iNOS and COX-2.

Figure 4:
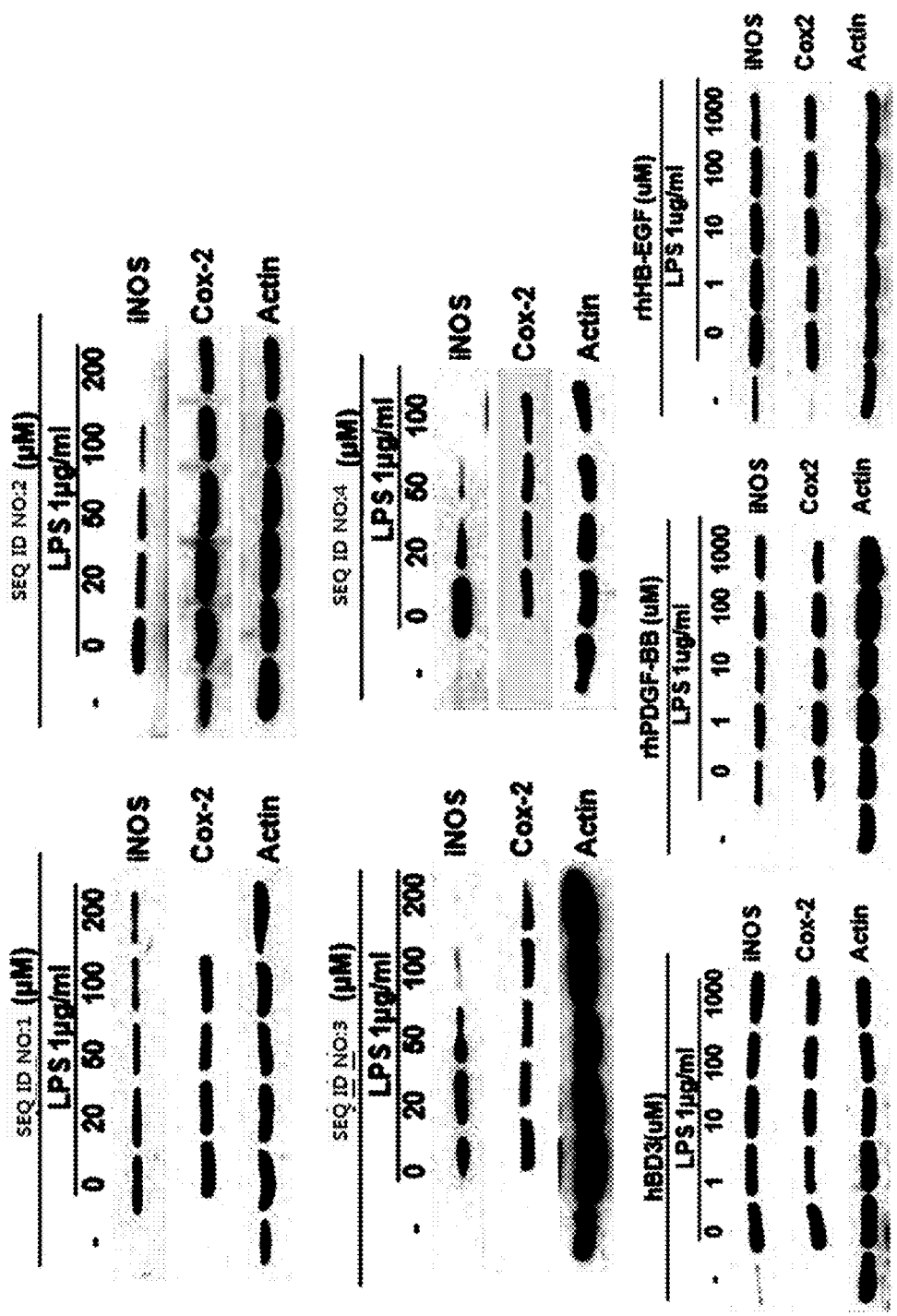
FIG. 4 shows the results of Western blot analysis of iNOS and COX-2.

As a result, as can be seen in FIG. 4, the peptides having the amino acid sequences of SEQ ID NOS: 1 to 4 inhibited the LPS-induced expression of iNOS and COX-2. However, hBD3, rhPDGF-BB and rhHB-EGF had no inhibitory effect on the expression of iNOS and COX-2.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

Industrial Applicability

As described above, the inventive peptide having antibacterial or anti-inflammatory activity can be used for the treatment of both dental infectious diseases, including periodontitis or peri-implantitis, and inflammations, including atopy, psoriasis or arthritis.

The invention claimed is:

1. An antibacterial composition containing the isolated peptide consisting of an amino acid sequence of SEQ ID NO: 2 as an active ingredient.

2. A composition for treating dental infectious disease containing the isolated peptide consisting of an amino acid sequence of SEQ ID NO: 2 as an active ingredient.

3. The composition of claim 2, wherein the dental infectious disease is selected from the group consisting of gingivitis, periodontitis, and peri-implantitis.

4. The composition of claim 2, wherein the composition is formulated in the form of a gel.

5. The composition of claim 2, further comprising a pharmaceutically acceptable carrier.

6. The composition of claim 5, wherein the composition is formulated in the form of a gel.

7. The composition of claim 1, wherein the composition contains the peptide in an amount of $10^{-3}$ to 1 part by weight.

8. The composition of claim 2, wherein the composition contains the peptide in an amount of $10^{-3}$ to 1 part by weight.

* * * * *

UNITED STATES PATENT AND TRADEMARK OFFICE
CERTIFICATE OF CORRECTION

| | |
|---|---|
| PATENT NO. | : 8,980,844 B2 |
| APPLICATION NO. | : 13/703565 |
| DATED | : March 17, 2015 |
| INVENTOR(S) | : Chong-Pyoung Chung et al. |

It is certified that error appears in the above-identified patent and that said Letters Patent is hereby corrected as shown below:

In the claims,

Column 7, line 22: "was added thereto and reacted for hour" should be -- was added thereto and reacted for 1 hour --.

Signed and Sealed this
Twelfth Day of May, 2015

Michelle K. Lee
*Director of the United States Patent and Trademark Office*